US010793865B2

(12) United States Patent
Phillips et al.

(10) Patent No.: US 10,793,865 B2
(45) Date of Patent: Oct. 6, 2020

(54) TRANSFERRABLE MECHANISM OF GENERATING INDUCIBLE, BAR DOMAIN PROTEIN-MEDIATED BACTERIAL OUTER MEMBRANE EXTENSIONS

(71) Applicant: The Government of the United States of America, as represented by the Secretary of the Navy, Arlington, VA (US)

(72) Inventors: Daniel A. Phillips, Washington, DC (US); Sarah M. Glaven, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/421,839

(22) Filed: May 24, 2019

(65) Prior Publication Data

US 2019/0367931 A1  Dec. 5, 2019

Related U.S. Application Data

(60) Provisional application No. 62/680,959, filed on Jun. 5, 2018.

(51) Int. Cl.
| | | |
|---|---|---|
| *C07H 21/00* | (2006.01) | |
| *C07H 21/02* | (2006.01) | |
| *A61K 39/00* | (2006.01) | |
| *C12N 15/74* | (2006.01) | |
| *C07K 14/195* | (2006.01) | |

(52) U.S. Cl.
CPC ............ *C12N 15/74* (2013.01); *C07K 14/195* (2013.01)

(58) Field of Classification Search
CPC ................................ A61K 39/00; A61K 39/02

USPC ....... 536/23.1, 23.7; 424/184.1, 185.1, 234.1
See application file for complete search history.

(56) References Cited

U.S. PATENT DOCUMENTS

2006/0166344 A1   7/2006   Pizza

OTHER PUBLICATIONS

Bird Bird LJ, Wang Z, Malanoski AP, et al. "Development of a Genetic System for Marinobacter atlanticus CP1 (sp. nov.), a Wax Ester Producing Strain Isolated From an Autotrophic Biocathode" Biocathode Front. Microbiol. 9:3176. doi: 10.3389/fmicb.2018.03176.
Hampton CM, Guerrero-Ferreira RC, Storms RE, et al. "The Opportunistic Pathogen Vibrio vulnificus Produces Outer Membrane Vesicles in a Spatially Distinct Manner Related to Capsular Polysaccharide." Front Microbiol. 2017;8:2177. Published Nov. 7, 2017. doi:10.3389/fmicb.2017.02177.
Sampath, V. , McCaig, W. D. and Thanassi, D. G. (2018), "Amino acid deprivation and central carbon metabolism regulate the production of outer membrane vesicles and tubes by Francisella." Molecular Microbiology, 107: 523-541. doi:10.1111/mmi.13897.
Subramanian et al. "Ultrastructure of Shewanella oneidensis MR-1 nanowires revealed by electron cryotomography." Proc Natl Acad Sci U S A. Apr. 3, 2018;115(14):E3246-E3255. doi: 10.1073/pnas.1718810115.
Nielsen, H. (2017). Predicting Secretory Proteins with SignalP. Protein Function Prediction: Methods and Protocols. D. Kihara. New York, NY, Springer New York: 59-73.

*Primary Examiner* — Rodney P Swartz
(74) *Attorney, Agent, or Firm* — US Naval Research Laboratory; Roy Roberts (57) ABSTRACT

A prokaryotic protein appearing to have a Bin/Amphiphysin/Rvs (BAR) domain, previously known in eukaryotes, has been identified. Expression of this protein causes formation of outer membrane extensions.

6 Claims, 7 Drawing Sheets

Specification includes a Sequence Listing.

TRANSFERRABLE MECHANISM OF GENERATING INDUCIBLE, BAR DOMAIN PROTEIN-MEDIATED BACTERIAL OUTER MEMBRANE EXTENSIONS

CROSS-REFERENCE TO RELATED APPLICATIONS

This application claims the benefit of U.S. Provisional Application 62/680,959 filed on Jun. 5, 2018, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375; (202) 767-7230; techtran@nrl.navy.mil, referencing NC 108123.

BACKGROUND

Bacteria produce outer membrane extensions (OMEs) or outer membrane vesicles (OMVs) in response to a variety of stimuli and stress conditions. Membrane extensions can be observed extending from single cells, as cell-cell connections between two cells, and as an elongated chain of several connected vesicles. Elaborate structures of outer membrane vesicles appearing as concentric rings can be observed extending from the outer membrane of the opportunistic pathogen *Vibrio vulnificus* (Hampton, Guerrero-Ferreira et al. 2017). The zoonotic pathogen *Francisella novicida* produces outer membrane tubules in response to cysteine deprivation (Sampath, McCaig et al. 2018). *Myxococcus xanthus* and *Shewanella oneidensis* generate membrane extensions that appear as vesicle chains ((Remis, Wei et al. 2014), (Gorby, Yanina et al. 2006), (Pirbadian, Barchinger et al. 2014)). In *S. oneidensis*, these membrane extensions are decorated with proteins implicated in extracellular electron transport (EET) (Subramanian, Pirbadian et al. 2018); however, the mechanism responsible for the formation of these outer membrane structures has yet to be elucidated.

Eukaryotic cells can induce complex, higher order membrane structures through interactions between lipids and membrane curvature-inducing proteins. Eukaryotic Bin/Amphiphysin/Rvs (BAR) domain proteins induce membrane curvature through electrostatic interactions between positively charged amino acids and negatively charged lipids. BAR domains can be accompanied by a membrane targeting domain, such as PX for phosphoinositide binding ((Seet and Hong 2006), (Itoh and De Camilli 2006)), in order to direct membrane curvature formation as specific sites, as is the case with sorting nexin BAR proteins (Lemmon 2008). The extent of accumulation of BAR domain proteins at a specific site can influence the degree of the resultant membrane curvature (Chen, Atefi et al. 2016), and tubulation events arise as a consequence of BAR domain multimerization in conjunction with lipid binding (Simunovic, Voth et al. 2015). BAR domain—lipid interactions also serve as a scaffold for membrane-localized cellular processes, such as actin binding through nWASP, signaling through small GTPases, and vesicular transport (Bassereau, Jin et al. 2018). While proteins have been discovered in prokaryotes that exhibit certain aspects of BAR domain function, such as the alpha helical protein SpoVM that is preferentially recruited to localized regions of high convex membrane curvature in *Bacillus subtilis* (Kim, Tyndall et al. 2017).

It is not believed that a functional BAR domain protein has been previously characterized as occurring in prokaryotes.

BRIEF SUMMARY

Described herein is a putative BAR domain-containing protein encoded within the *S. oneidensis* MR-1 genome. Through molecular genetics techniques, it can be employed for reliable induce expression of outer membrane extensions in several bacterial species. The aerobically inducible outer membrane extensions resemble the outer membrane vesicle chains described previously (Subramanian, Pirbadian et al. 2018).

In a first embodiment, an expression plasmid comprises an inducible promoter and a nucleic acid sequence encoding SEQ ID No. 1 (termed either SO_1507 or BdpA for BAR Domain-like Protein A)

(MRTAAVISMLLFGVLTSVNASAKDNELVFASDFEGNRLSQPWSWIMGCQ
FDGAEPHSGESALLCAEGNSSIVSKYPVSEAGLLEFWVKTQNIQTQYRIN
VLTSPVLKLDAQWQNVALIDVTPGTNEYLAHRVSIDDPSRQYIRLDIEAI
NGPISLDDLTLDKIRLDIALQKNEQKIIGGILDKLKEDKNYEVQAESFRT
LGKNYAAQLESQRQYLEYSNAIYSSITFVLATSERNKMSNPLGYNTFRSV
LTDAKRIASPIQQARLGSMVKPFGDLATATLNVVSAGAYSAFAEPFKSFL
AATFDRSNYDNSDLSRSDKKFAEENGLKIYQQAERFMAEIEKELQQVTAL
DNDLVSMQKNLDNFRKDLDKHLRSYLQHASIARTPENYSKVMSKDEQTRS
EIMADVNTNISAKAEALLASNSNAELVQYMIKTTEKMDEFQEFKERFNQI
TSAMLTFYDRFERSIAAEQNPFTDPSDRAVWEQHAQSARNYIRQSKEAFT
KAFM).

In another embodiment, a method of causing outer membrane extensions in bacteria includes providing the expression plasmid of the first embodiment; transforming the bacteria with the expression plasmid; and then inducing expression of BdpA, thereby causing outer membrane extensions in the bacteria.

BRIEF DESCRIPTION OF THE DRAWINGS

FIGS. 4A-4C are cryo-electromicrographic images of induction with aerobic expression of SO_1507 in *S. oneidensis* MR-1. FIG. 4A shows that uninduced *S. oneidensis*

MR-1 p452_BAR cells exhibited a uniform outer membrane phenotype, while induced cells in FIG. 4B were decorated with outer membrane extensions (highlighted area enlarged in FIG. 4C). The extensions display a "pearls-on-a-string" morphology described previously with periodically interspersed "junction densities" (FIG. 4C).

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

A prokaryotic protein appearing to have a Bin/Amphiphysin/Rvs (BAR) domain, previously known in eukaryotes, has been identified. Expression of this protein causes formation of outer membrane extensions.

EXAMPLES

Methods

S. oneidensis strains were grown aerobically in Luria Bertani (LB) media at 30° C. with 50 µg/mL kanamycin when maintaining the plasmid. To observe membrane extensions, cells were centrifuged and resuspended in a defined media comprised of 30 mM Pipes, 60 mM sodium DL-lactate as an electron donor, 28 mM NH4Cl, 1.34 mM KCl, 4.35 mM NaH2PO4, 7.5 mM NaOH, 30 mM NaCl, 1 mM MgCl2, 1 mM CaCl2, and 0.05 mM ferric nitrilotriacetic acid (Pirbadian, Barchinger et al. 2014). Marinobacter atlanticus CP1 strains were grown in BB media at 30° C. with 100 µg/mL kanamycin to maintain the plasmids as described previously (Bird, Wang et al. 2018). For induction assays, cells were grown in precultures overnight and diluted to an $OD_{600}$ of 0.1 before induction with 12.5 µM 2,4-diacetylphloroglucinol (DAPG). At 2 hours post-induction, 100 µL aliquots of cells were labeled with 0.5 µg/mL FM 4-64 (Thermo Fischer). Labeled cells were sealed on cover glass mounted onto glass slides with clear acrylic nail polish for 2 minutes before imaging.

Inducible BDPA expression plasmids were constructed for use in S. oneidensis MR-1, M. atlanticus CP1, and E. coli BL21(DE3) using the 2,4-diacetylphloroglucinol-inducible phlF sensor from the Marionette sensor library (Meyer, Segall-Shapiro et al. 2018). The yellow fluorescence protein (YFP) cassette from pAJM452 was replaced by the gene encoding ORF SO_1507 (that is, BdpA) by Gibson assembly, and the promoter/repressor construct was cloned into the broad range vector pBBR1-MCS2 for conjugation into recipient organisms. The resulting plasmid was given the name p452_BAR. The Gibson assembly reactions were electroporated into E. coli Top10 DH5α or BL21(DE3) cells, and the sequences were confirmed through Sanger sequencing. Plasmid constructs were chemically transformed into conjugation-competent E. coli WM3064 cells for conjugative transfer into the recipient bacterial strains of S. oneidensis MR-1 and M. atlanticus CP1. Generation of scarless ΔSO_1507 knockout mutant strains of S. oneidensis was performed by combining 1 kilobase fragments flanking upstream and downstream from ORF SO_1507 by Gibson assembly into the pSMV3 suicide vector. The resultant plasmid pSMV3_1507KO was transformed into E. coli UQ950 cells for propagation. Plasmid sequences were confirmed by Sanger sequencing after purification from the E. coli UQ950 pSMV3_1507KO cells before chemical transformation into E. coli WM3064 as before.

The conserved domain database search tool (CDD-search)(NCBI) was used to identify the protein containing the putative BAR domain. Secondary structure characteristics were identified by a hidden Markov model (HMM), and protein localization was predicted by SignalP (Nielsen 2017).

For in vivo imaging of outer membrane extension production, S. oneidensis strains were grown in LB media overnight then washed 2× and diluted to an $OD_{600}$ of 0.3 in 1 mL fresh media with appropriate antibiotics. M. atlanticus CP1 strains were grown as above, but in BB medium with appropriate antibiotics. E. coli BL21(DE3) cells were grown in LB with 50 µg/mL kanamycin. Diluted cells were induced with 12.5 µM DAPG for 1 hour at 30° C. with 200 RPM shaking agitation for outer membrane extension production. 100 µL of each culture was labeled with 0.5 µg/mL FM 4-64 (Thermo Fischer) to visualize the cell membranes. After staining, 10 µL of the labeled cell suspension was gently pipetted onto 22×22 mm No. 1 cover glass (VWR) and sealed onto glass slides with clear acrylic nail polish. For visualization of WT and ΔSO_1507 outer membrane extension production, cells from overnight LB culture were washed twice and resuspended in a Shewanella defined medium as reported previously (Gorby, Yanina et al. 2006) at an $OD_{600}$ of 0.1. Cells were labeled with FM 4-64 and sealed onto glass slides as before. Confocal images were taken by a Zeiss LSM 800 (Zeiss) microscope with a 63× magnification, 1.4 numerical aperture objective at 5× zoom.

Cells from overnight starter cultures were diluted to an OD600=0.1 to aid in visualizing single cells. 4 µL of each cell culture was spotted onto Quantifoil square mesh 200 EM grids (Electron Microscopy Sciences, Fort Washington, Pa.), blotted for 3-3.5 seconds, and plunge frozen in liquid ethane (Leica EM plunge freezer). Grids were kept in liquid N2 at <−170° C. before loading into the FEI TITAN electron microscope (FEI).

Results

Figure 1:
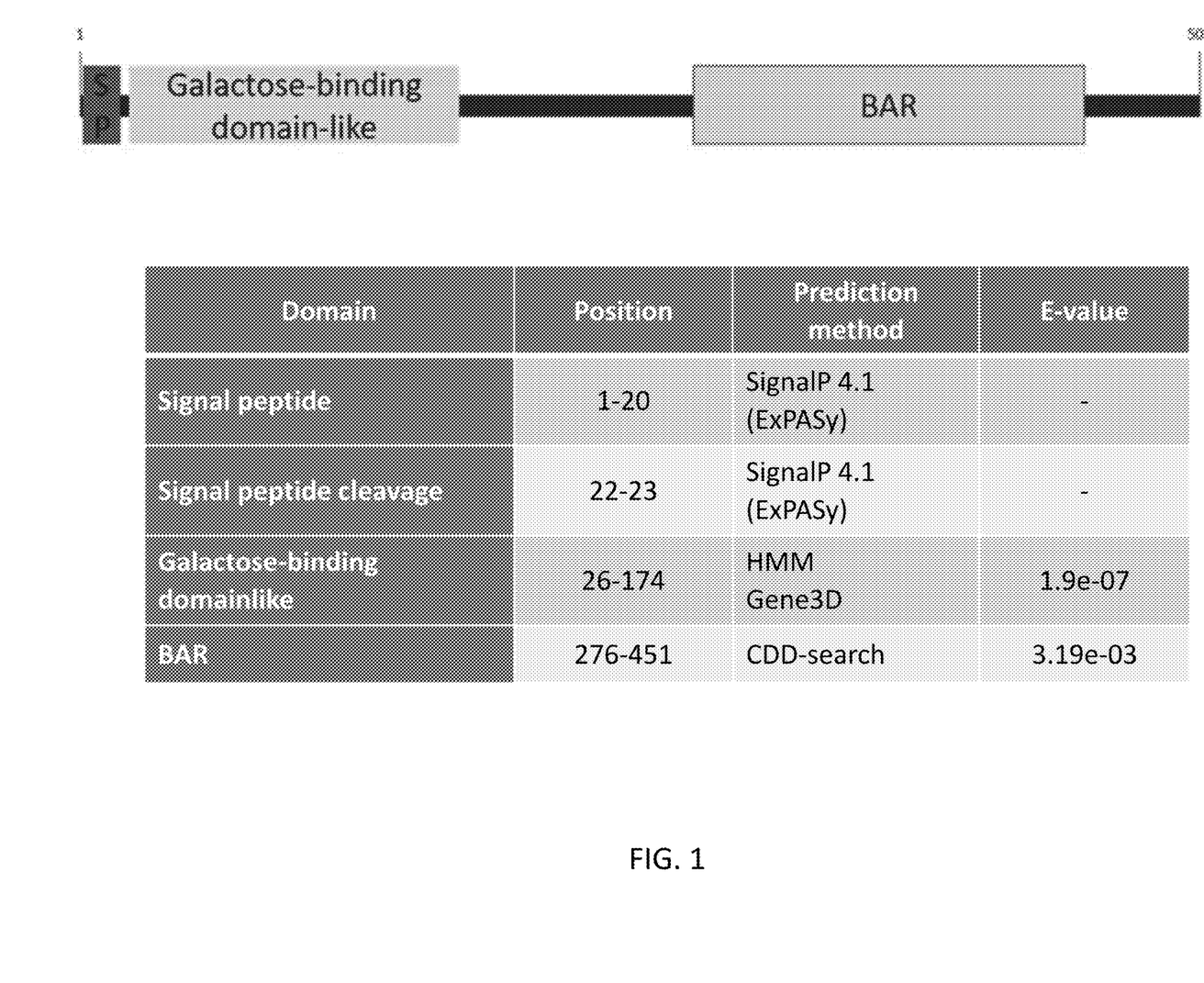
FIG. 1 illustrates BAR domain protein prediction: The putative BAR domain-containing protein BdpA was identified by CDD-search (NCBI). The N-terminal signal peptide (SP) suggests the protein is likely secreted either into the periplasm or outside the cell. The predicted galactose-binding domain-like region may facilitate binding to the outer membrane lipopolysaccharides.

A carboxy-terminal BAR domain was predicted to be encoded by the S. oneidensis open reading frame SO_1507 as depicted in FIG. 1. The protein was named BdpA for BAR Domain-like Protein A. The protein has an N-terminal signal peptide with predicted cleavage sites between amino acids 22-23, suggesting it is exported to the periplasm or outer membrane. A galactose-binding domain-like region positioned immediately downstream of the signal peptide supports lipid targeting activity seen in other BAR domain proteins, such as the eukaryotic sorting nexins (Carlton, Bujny et al. 2004), which have PX domains that bind phosphoinositides. The C-terminal BAR domain is predicted to span from AA 276-451; however, since the identification of the protein is based upon homology to the BAR domain consensus sequence (cd07307), it is possible that the BAR domain region extends beyond these bounds.

Since S. oneidensis membrane extensions are only reliably observed during anaerobic growth when attached to a surface, it was suspected that placing BDPA under inducible control would result in aerobically expressed outer membrane extensions. The Marionette sensor library contains plasmids with low background expression and a high degree of sensitivity, providing tightly regulated, tunable control of protein expression (Meyer, Segall-Shapiro et al. 2018). To test the theory that BDPA was sufficient to induce membrane extensions in S. oneidensis, the plasmid p452_BAR was constructed containing BDPA under control of a DAPG-inducible promoter from the Marionette sensor library. Membrane extensions from DAPG induced S. oneidensis p452_BAR cultures could be observed immediately upon sealing onto the cover glass following a 1-2 h induction time, ranging between 1-7 extensions per cell. Uninduced cultures did not display similar membrane extension production until beyond 45 minutes sealed onto cover glass, suggesting that BDPA is sufficient to promote the formation of these membrane structures.

Figure 2A:
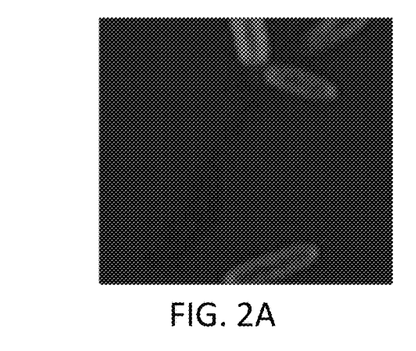
FIGS. 2A-2G show outer membrane extension in the bacterial species *S. oneidensis* (FIGS. 2A through 2D) and *M. atlanticus* (FIGS. 2E through 2G).
Figure 2B:
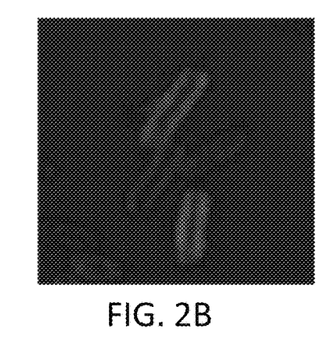
Figure 2C:
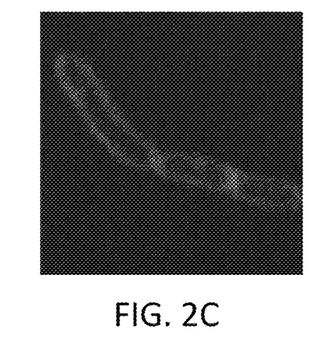
Figure 2D:
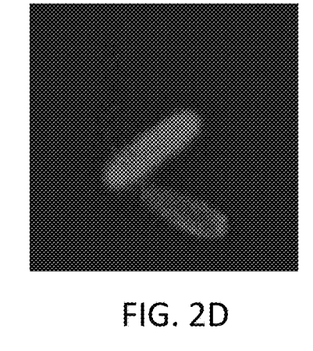
Figure 2E:
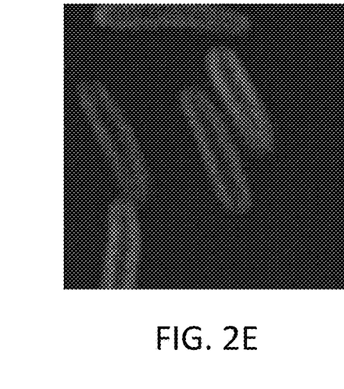
Figure 2F:
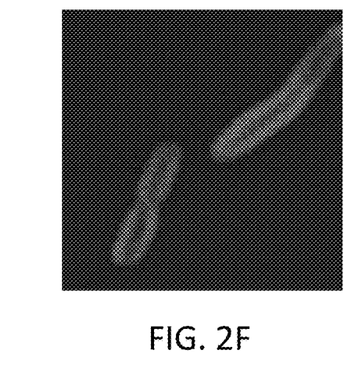
Figure 2G:
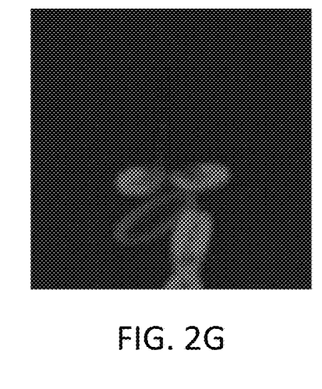

FIGS. 2A-2G provide photomicrographic evidence of the role of BDPA in outer membrane extension, with cell membranes labeled with the membrane-specific dye FM 4-64 for confocal microscopy. Normally, S. oneidensis does not produce OMEs under aerobic conditions. The wild-type (WT) and ΔSO_1507 varieties of S. oneidensis both produce membrane extensions when sealed anaerobically for two hours, depicted in FIGS. 2A and 2B, respectively. However strains containing the inducible BAR protein vector p452_BAR displayed membrane extensions immediately after 1 hour induction from aerobic, shaking culture in both S. oneidensis MR-1 (FIG. 2D) and M. atlanticus CP1 (FIG. 2G). FIGS. 2C and 2F are images of uninduced S. oneidensis MR-1 and M. atlanticus CP1, respectively, each with p452_BAR. FIG. 2E shows the wild-type M. atlanticus.

Figure 3A:
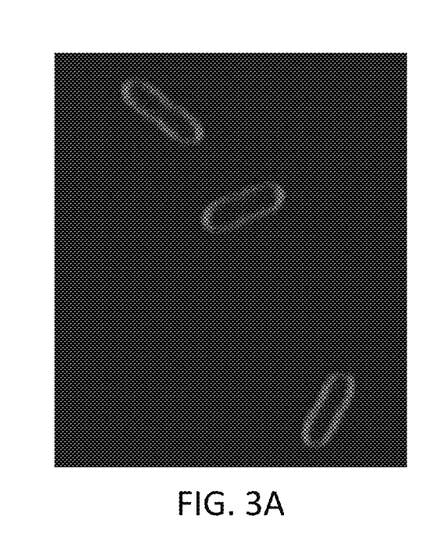
FIGS. 3A-3C show outer membrane extension production in *E. coli* BL21 (DE3) cells after induction of BdpA, depicting wild-type bacteria (FIG. 3A), uninduced bacteria carrying p452_BAR (FIG. 3B), and induced bacteria carrying p452_BAR (FIG. 3C).
Figure 3B:
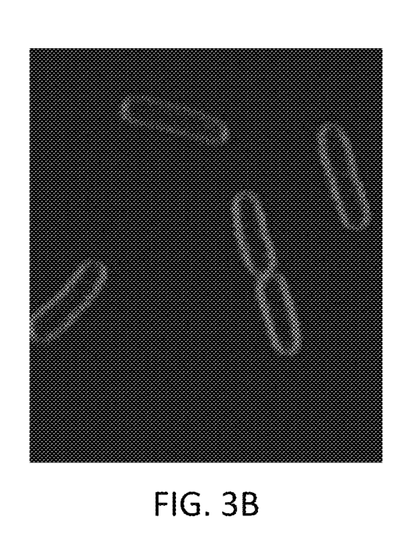

Previous studies have shown extracellular extensions of the S. oneidensis outer membrane can be detected within 90-120 minutes when attached to a surface in anaerobic conditions (Pirbadian, Barchinger et al. 2014). Live-cell imaging of S. oneidensis strains labelled with the lipophilic dye FM4-64 was performed to recapitulate the membrane extension phenotype in wildtype MR-1 cells, as well as to note phenotypic differences in the ΔSO_1507 strain (FIG. 3a, 3b). After 3 hours sealed on glass slides, both WT and ΔSO_1507 produced membrane extensions.

Figure 3C:
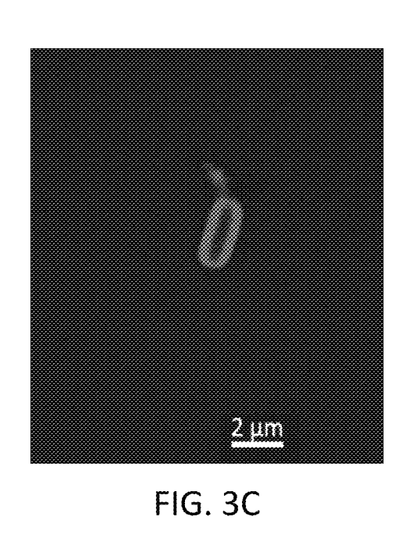

Expanding on the work with S. oneidensis, other bacterial species were examined. E. coli are not observed to produce outer membrane extensions when grown in planktonic, shaking culture (FIG. 3a). Likewise, uninduced E. coli cells harboring the p452_BAR plasmid did not produce membrane extensions (FIG. 3b). However, when expression of BDPA is induced in E. coli BL21(DE3) cells, outer membrane extensions could be observed extending from the cells (FIG. 3c).

Figure 4A:
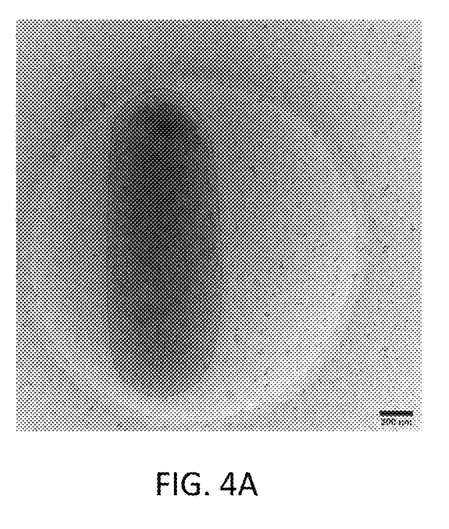
Figure 4B:
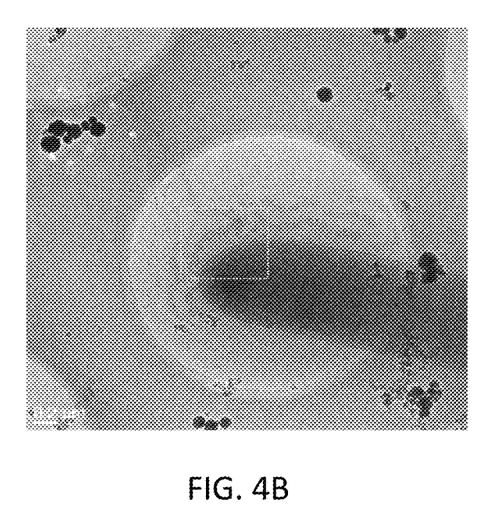
Figure 4C:
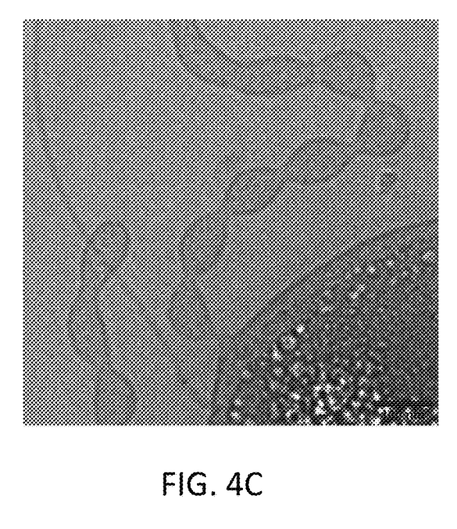

Cryo-electron microscopy is a powerful tool for resolving ultrastructural cell morphologies while preserving the native physiological states without fixatives. Recently, cryo-EM tomography described the S. oneidensis membrane extensions observed under anaerobic conditions as "beads-on-a-string" with junction densities located at intervals along the outer membrane extensions (Subramanian, Pirbadian et al. 2018). In order to examine the ultrastructural characteristics of the inducible BDPA outer membrane extensions, cells were induced as before, but were plunge frozen at 2 hours post induction to preserve the native state of the outer membrane architecture. Induced cells displayed tubules at a frequency of 1/20 cells examined, likely due to shear forces during blotting. Outer membrane extensions had a diameter of approximately about 50-60 nm, consistent with BAR domain mediated membrane tubules (Daumke, Roux et al. 2014). Uninduced cells were predominately devoid of membrane extensions or irregular outer membrane curvature. Results are shown in FIGS. 4A-4C.

Figure 5A:
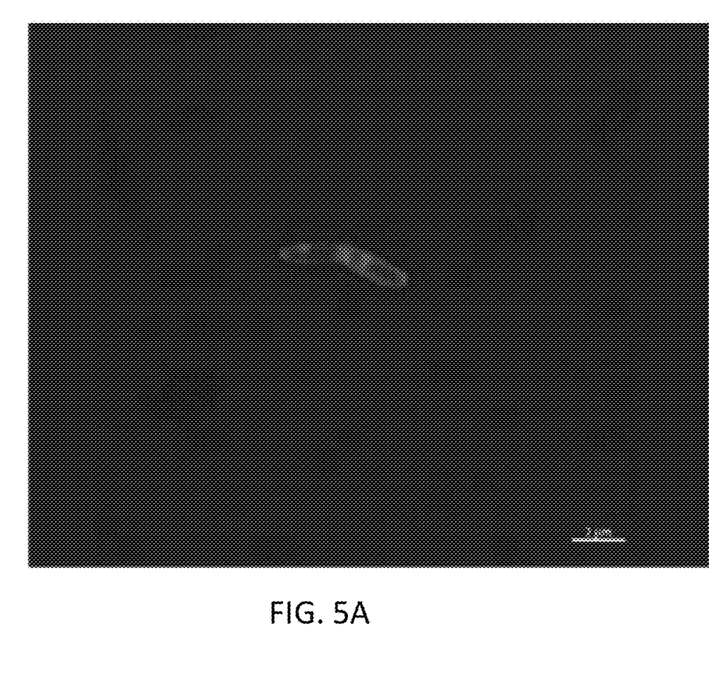
FIGS. 5A and 5B show aerobic induction of S. oneidensis p452_BAR cultures. Uninduced S. oneidensis p452_BAR cultures (FIG. 5A) were predominately devoid of elongated membrane extensions. Induced p452_BAR cells (FIG. 5B) had membrane extensions that were observable immediately upon sealing onto glass slides following aerobic induction. Induced cells displayed between 1-7 extensions per cell. Scale=2 µm.
Figure 5B:
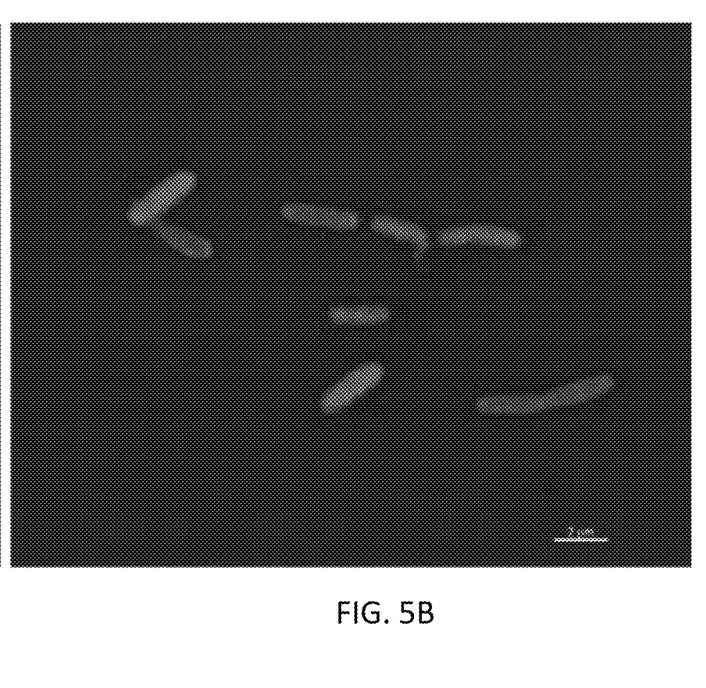
Figure 6A:
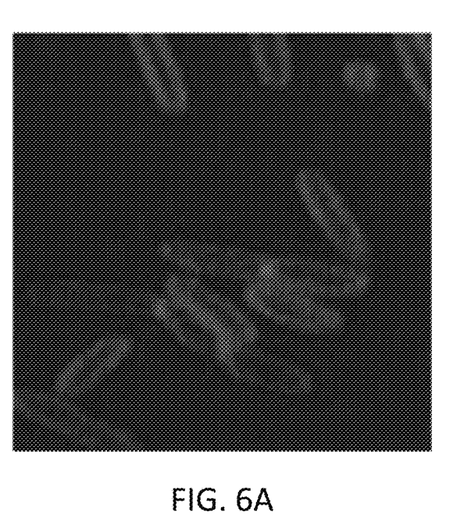
FIGS. 6A-6C show aerobic induction of outer membrane extensions in M. atlanticus CP. M. atlanticus CP1 WT (FIG. 6A) and uninduced CP1 p452_BAR (FIG. 6B) cells did not produce outer membrane extensions. In induced CP1 p452_BAR samples (FIG. 6C), membrane extensions are observable immediately upon sealing onto glass slides. Induced cells displayed membrane curvature phenotypes including dynamic S. oneidensis-like outer membrane extensions. Scale=2 µm FIG. 7A provides a signal peptide prediction of BDPA suggesting periplasmic or outer membrane localization.
Figure 6B:
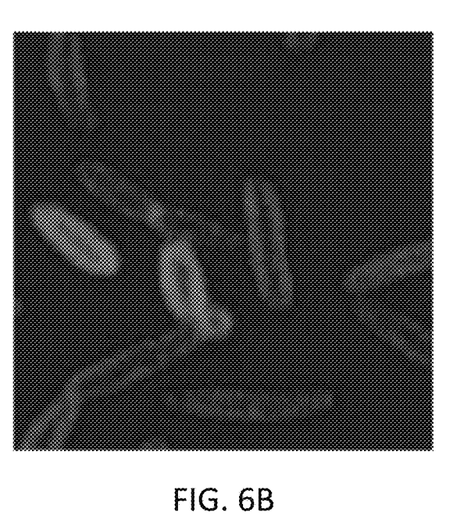
Figure 6C:
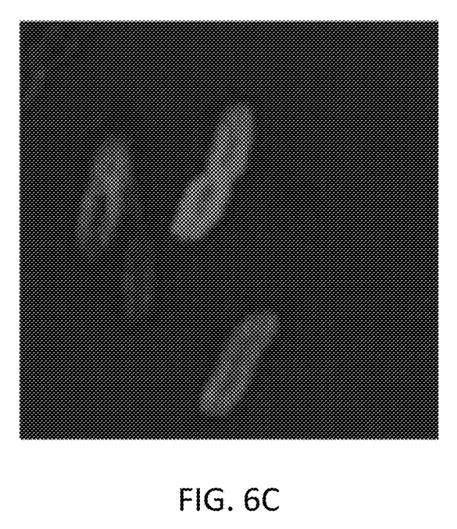
Figure 7A:
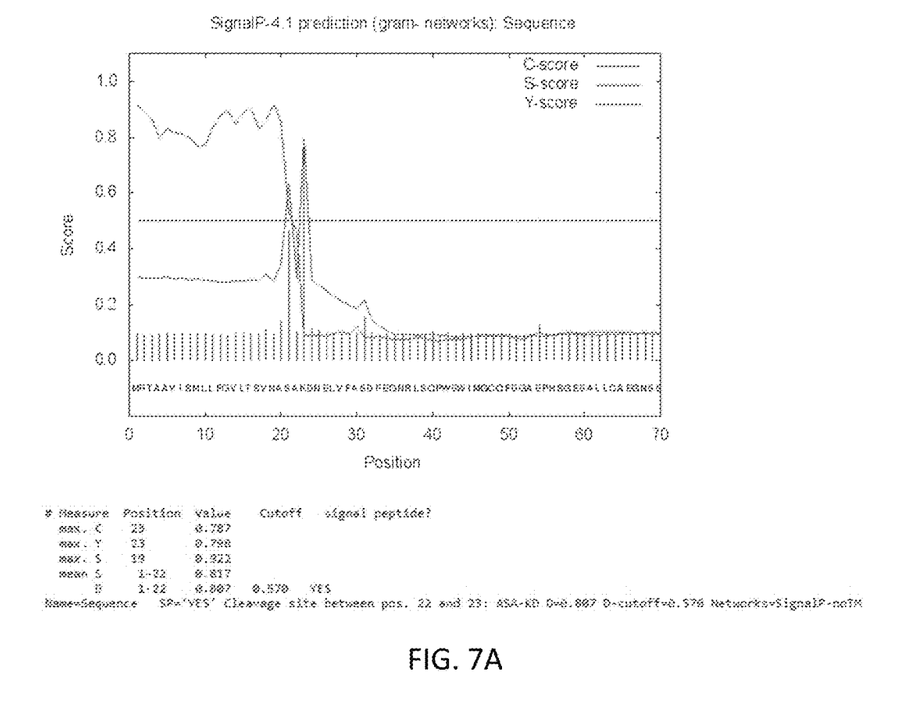
Figure 7B:
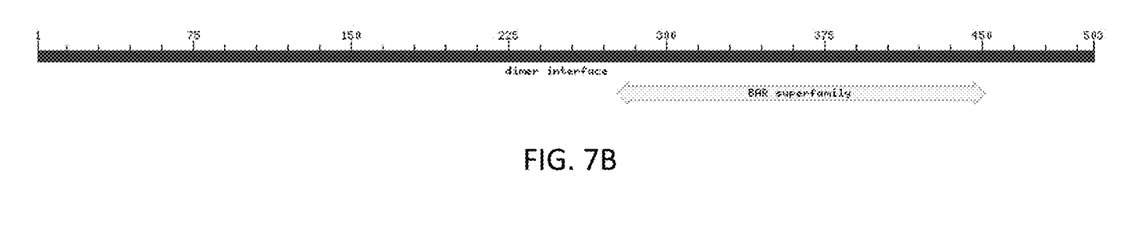
FIG. 7B shows amino acid positions of the BAR domain region of BDPA.

The putative BAR domain protein was further tested for the ability to confer the inducible membrane extension phenotype in another organism. The p452_BAR vector was transformed into M. atlanticus CP1, an organism not known to produce membrane extensions under normal growth conditions. After 2 hours of aerobic induction in shaking culture with 12.5 µM DAPG, M. atlanticus p452_BAR cultures produced membrane extensions similar to those observed in WT and p452_BAR induced S. oneidensis. Further, after a 2 hour induction the cell morphology of M. atlanticus was varied when compared to WT cells, including cells that were smaller, comma-shaped, or displayed longer, inflexible membrane extensions. Results are shown in FIGS. 5A and 5B. Thus, BDPA provides a transferrable mechanism for membrane remodeling capability in vivo.

Further Embodiments and Applications

Bacterial OMVs are antigenic, non-infectious, and may elicit a protective immune response when used in vaccines. With an inducible mechanism of OMV production, vaccines could be developed for target pathogens utilizing the array of the bacteria's own membrane-bound surface proteins, leading to new vaccines against organisms for which none currently exist.

In Shewanella, naturally-forming OMEs are suspected to play a role in conductivity of electrons through a biofilm grown on a surface. With this mechanism, conductive OMEs can be produced on-demand, allowing for the development of living material transistors and long range extracellular electron transfer.

A possibility exists that this technology could be adapted for use in living material sensors, for example those integrated into marine devices.

It is believed that controlled (e.g., inducible) expression of a BAR domain-containing protein, for example BDPA, can be used for bacterial membrane sculpting for synthetic biology applications. This might be done in various species of bacteria, for example Gram-negative bacteria. With inducible BDPA on a broad range vector, controlled membrane sculpting could conceivably be achieved in any Gram-negative bacteria with an established genetics system. This affords opportunities for the advancement of bacterial membrane-derived soft materials production, including, but not limited to, vaccine development, novel scaffolding materials for synthesis applications, localized delivery of interspecies cargo, and on-demand cell-cell contact.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Bassereau, P., R. Jin, T. Baumgart, M. Deserno, R. Dimova, V. A. Frolov, P V. Bashkirov, H. Grubmuiller, R. Jahn, H. J. Risselada, L. Johannes, M. M. Kozlov, R. Lipowsky, T. J. Pucadyil, W E Zeno, J. C. Stachowiak, D. Stamou, A. Breuer, L. Lauritsen, C. Simon, C. Sykes, G. A. Voth and T. R. Weikl (2018). "The 2018 biomembrane curvature and remodeling roadmap." Journal of Physics D: Applied Physics 51(34): 343001.

Bird, L. J., Z. Wang, A. P. Malanoski, E. L. Onderko, B. J. Johnson, M. H. Moore, D. A. Phillips, B. J. Chu, J. E Doyle, B. J. Eddie and S. M. Glaven (2018). "Development of a Genetic System for *Marinobacter atlanticus* CP1 (sp. nov.), a Wax Ester Producing Strain Isolated From an Autotrophic Biocathode." Front Microbiol 9: 3176.

Carlton, J., M. Bujny, B. J. Peter, V. M. Oorschot, A. Rutherford, H. Mellor, J. Klumperman, H. T. McMahon and P. J. Cullen (2004). "Sorting nexin-1 mediates tubular endosome-to-TGN transport through coincidence sensing of high-curvature membranes and 3-phosphoinositides." Curr Biol 14(20): 1791-1800.

Chen, Z., E. Atefi and T. Baumgart (2016). "Membrane Shape Instability Induced by Protein Crowding." Biophys J 111(9): 1823-1826.

Daumke, O., A. Roux and V. Haucke (2014). "BAR domain scaffolds in dynamin-mediated membrane fission." Cell 156(5): 882-892.

Gorby, Y. A., S. Yanina, J. S. McLean, K. M. Rosso, D. Moyles, A. Dohnalkova, T. J. Beveridge, I. S. Chang, B. H. Kim, K. S. Kim, D. E. Culley, S. B. Reed, M. F Romine, D. A. Saffarini, E. A. Hill, L. Shi, D. A. Elias, D. W Kennedy, G. Pinchuk, K. Watanabe, S. Ishii, B. Logan, K. H. Nealson and J. K. Fredrickson (2006). "Electrically conductive bacterial nanowires produced by *Shewanella oneidensis* strain MR-1 and other microorganisms." Proc Natl Acad Sci USA 103(30): 11358-11363.

Hampton, C. M., R. C. Guerrero-Ferreira, R. E. Storms, J. V. Taylor, H. Yi, P. A. Gulig and E. R. Wright (2017). "The Opportunistic Pathogen *Vibrio vulnificus* Produces Outer Membrane Vesicles in a Spatially Distinct Manner Related to Capsular Polysaccharide." Front Microbiol 8: 2177.

Itoh, T. and P. De Camilli (2006). "BAR, F-BAR (EFC) and ENTH/ANTH domains in the regulation of membrane-cytosol interfaces and membrane curvature." Biochim Biophys Acta 1761(8): 897-912.

Kim, E. Y., E. R. Tyndall, K. C. Huang, E Tian and K. S. Ramamurthi (2017). "Dash-and-Recruit Mechanism Drives Membrane Curvature Recognition by the Small Bacterial Protein SpoVM." Cell Syst 5(5): 518-526 e513.

Lemmon, M. A. (2008). "Membrane recognition by phospholipid-binding domains." Nat Rev Mol Cell Biol 9(2): 99-111.

Meyer, A. J., T. H. Segall-Shapiro, E. Glassey, J. Zhang and C. A. Voigt (2018). "*Escherichia coli* "Marionette" strains with 12 highly optimized small-molecule sensors." Nature Chemical Biology.

Nielsen, H. (2017). Predicting Secretory Proteins with SignalP. Protein Function Prediction: Methods and Protocols. D. Kihara. New York, N.Y., Springer New York: 59-73.

Pirbadian, S., S. E. Barchinger, K. M. Leung, H. S. Byun, Y Jangir, R. A. Bouhenni, S. B. Reed, M. E Romine, D. A. Saffarini, L. Shi, Y A. Gorby, J. H. Golbeck and M. Y. El-Naggar (2014). "*Shewanella oneidensis* MR-1 nanowires are outer membrane and periplasmic extensions of the extracellular electron transport components." Proc Natl Acad Sci USA 111(35): 12883-12888.

Remis, J. P., D. Wei, A. Gorur, M. Zemla, J. Haraga, S. Allen, H. E. Witkowska, J. W Costerton, J. E. Berleman and M. Auer (2014). "Bacterial social networks: structure and composition of *Myxococcus xanthus* outer membrane vesicle chains." Environ Microbiol 16(2): 598-610.

Sampath, V., W D. McCaig and D. G. Thanassi (2018). "Amino acid deprivation and central carbon metabolism regulate the production of outer membrane vesicles and tubes by *Francisella*." Mol Microbiol 107(4): 523-541.

Seet, L. E and W Hong (2006). "The Phox (PX) domain proteins and membrane traffic." Biochim Biophys Acta 1761(8): 878-896.

Simunovic, M., G. A. Voth, A. Callan-Jones and P. Bassereau (2015). "When Physics Takes Over: BAR Proteins and Membrane Curvature." Trends Cell Biol 25(12): 780-792.

Subramanian, P., S. Pirbadian, M. Y. El-Naggar and G. J. Jensen (2018). "Ultrastructure of *Shewanella oneidensis* MR-1 nanowires revealed by electron cryotomography." Proc Natl Acad Sci USA 115(14): E3246-E3255.

What is claimed is:

1. A method of causing outer membrane extensions in bacteria, the method comprising:
   providing an expression plasmid comprising an inducible promoter and a nucleic acid encoding SEQ ID No. 1;
   transforming the bacteria with the expression plasmid; and then
   inducing expression of SEQ ID No. 1, thereby causing outer membrane extensions in the bacteria.

2. The method of claim 1, wherein the bacteria is Gram-negative.

3. The method of claim 2, wherein the bacteria is selected from the group consisting of *Shewanella oneidensis*, *Marinobacter atlanticus*, and *Escherichia coli*.

4. The method of claim 1, wherein the bacteria are grown aerobically.

5. An expression plasmid comprising an inducible promoter and a nucleic acid sequence encoding SEQ ID No. 1.

6. The expression plasmid of claim 5 wherein the inducible promoter is phlF.

* * * * *

SEQUENCE LISTING

<160> NUMBER OF SEQ ID NOS: 1

<210> SEQ ID NO 1
<211> LENGTH: 503
<212> TYPE: PRT
<213> ORGANISM: Shewanella oneidensis

<400> SEQUENCE: 1

```
Met Arg Thr Ala Ala Val Ile Ser Met Leu Leu Phe Gly Val Leu Thr
1               5                   10                  15

Ser Val Asn Ala Ser Ala Lys Asp Asn Glu Leu Val Phe Ala Ser Asp
                20                  25                  30

Phe Glu Gly Asn Arg Leu Ser Gln Pro Trp Ser Trp Ile Met Gly Cys
            35                  40                  45

Gln Phe Asp Gly Ala Glu Pro His Ser Gly Glu Ser Ala Leu Leu Cys
50                  55                  60

Ala Glu Gly Asn Ser Ser Ile Val Ser Lys Tyr Pro Val Ser Glu Ala
65                  70                  75                  80

Gly Leu Leu Glu Phe Trp Val Lys Thr Gln Asn Ile Gln Thr Gln Tyr
                85                  90                  95

Arg Ile Asn Val Leu Thr Ser Pro Val Leu Lys Leu Asp Ala Gln Trp
            100                 105                 110

Gln Asn Val Ala Leu Ile Asp Val Thr Pro Gly Thr Asn Glu Tyr Leu
        115                 120                 125

Ala His Arg Val Ser Ile Asp Asp Pro Ser Arg Gln Tyr Ile Arg Leu
130                 135                 140

Asp Ile Glu Ala Ile Asn Gly Pro Ile Ser Leu Asp Asp Leu Thr Leu
145                 150                 155                 160

Asp Lys Ile Arg Leu Asp Ile Ala Leu Gln Lys Asn Glu Gln Lys Ile
                165                 170                 175

Ile Gly Gly Ile Leu Asp Lys Leu Lys Glu Asp Lys Asn Tyr Glu Val
            180                 185                 190

Gln Ala Glu Ser Phe Arg Thr Leu Gly Lys Asn Tyr Ala Ala Gln Leu
        195                 200                 205

Glu Ser Gln Arg Gln Tyr Leu Glu Tyr Ser Asn Ala Ile Tyr Ser Ser
210                 215                 220

Ile Thr Phe Val Leu Ala Thr Ser Glu Arg Asn Lys Met Ser Asn Pro
225                 230                 235                 240

Leu Gly Tyr Asn Thr Phe Arg Ser Val Leu Thr Asp Ala Lys Arg Ile
                245                 250                 255

Ala Ser Pro Ile Gln Gln Ala Arg Leu Gly Ser Met Val Lys Pro Phe
            260                 265                 270

Gly Asp Leu Ala Thr Ala Thr Leu Asn Val Val Ser Ala Gly Ala Tyr
        275                 280                 285

Ser Ala Phe Ala Glu Pro Phe Lys Ser Phe Leu Ala Thr Phe Asp
290                 295                 300

Arg Ser Asn Tyr Asp Asn Ser Asp Leu Ser Arg Ser Asp Lys Lys Phe
305                 310                 315                 320

Ala Glu Glu Asn Gly Leu Lys Ile Tyr Gln Gln Ala Glu Arg Phe Met
                325                 330                 335

Ala Glu Ile Glu Lys Glu Leu Gln Gln Val Thr Ala Leu Asp Asn Asp
            340                 345                 350

Leu Val Ser Met Gln Lys Asn Leu Asp Asn Phe Arg Lys Asp Leu Asp
        355                 360                 365

Lys His Leu Arg Ser Tyr Leu Gln His Ala Ser Ile Ala Arg Thr Pro
370                 375                 380

Glu Asn Tyr Ser Lys Val Met Ser Lys Asp Glu Gln Thr Arg Ser Glu
385                 390                 395                 400

Ile Met Ala Asp Val Asn Thr Asn Ile Ser Ala Lys Ala Glu Ala Leu
```

```
                    405                 410                 415
Leu Ala Ser Asn Ser Asn Ala Glu Leu Val Gln Tyr Met Ile Lys Thr
            420                 425                 430

Thr Glu Lys Met Asp Glu Phe Gln Glu Phe Lys Glu Arg Phe Asn Gln
        435                 440                 445

Ile Thr Ser Ala Met Leu Thr Phe Tyr Asp Arg Phe Glu Arg Ser Ile
    450                 455                 460

Ala Ala Glu Gln Asn Pro Phe Thr Asp Pro Ser Asp Arg Ala Val Trp
465                 470                 475                 480

Glu Gln His Ala Gln Ser Ala Arg Asn Tyr Ile Arg Gln Ser Lys Glu
            485                 490                 495

Ala Phe Thr Lys Ala Phe Met
            500
```